United States Patent [19]

Trybulski et al.

[11] Patent Number: 5,128,483

[45] Date of Patent: Jul. 7, 1992

[54] DIBROMOVINYL AND ACETYLENE-1-PYRROLIDINECARBOXYLIC ACID INTERMEDIATES

[75] Inventors: Eugene J. Trybulski, Park Ridge, N.J.; Richard H. Kramss, Newburgh, N.Y.

[73] Assignee: American Cyanamid Company, Wayne, N.J.

[21] Appl. No.: 697,173

[22] Filed: May 8, 1991

Related U.S. Application Data

[60] Continuation of Ser. No. 602,565, Oct. 9, 1990, abandoned, which is a division of Ser. No. 382,813, Jul. 19, 1989, Pat. No. 5,001,142.

[51] Int. Cl.⁵ .................. C07D 207/06; C07D 207/08
[52] U.S. Cl. .................................................. 548/531
[58] Field of Search .......................................... 548/531

[56] References Cited

U.S. PATENT DOCUMENTS 5,001,142  3/1991  Trybulski et al. .............. 548/579 X
5,036,153  7/1991  Braish et al. .................... 548/531 X

*Primary Examiner*—Joseph Paul Brust
*Attorney, Agent, or Firm*—Kenneth J. Dow

[57] ABSTRACT

Compounds of the formula:

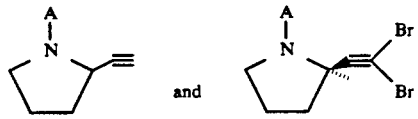

and wherein A is t-butoxy carbonyl, which compounds are useful as intermediates for preparing 1-Substituted-2-(3-amino-1-propynyl)pyrrolidine derivatives having cholinergic agonist activity.

4 Claims, No Drawings

DIBROMOVINYL AND ACETYLENE-1-PYRROLIDINECARBOXYLIC ACID INTERMEDIATES this is a continuation of co-pending application Ser. No. 07/602,565, filed on Oct. 9, 1990, now abandoned, which is a divisional of application Ser. No. 07/382,813, filed on Jul. 19, 1989, now U.S. Pat. No. 5,001,142."

BACKGROUND OF THE INVENTION

The present invention relates to novel (3-amino-1-propynyl)pyrrolidine compounds, pharmaceutical compositions containing the compounds and to the use of the compounds for the treatment of central cholinergic disfunction.

Senile Dementia of the Alzheimer's Type (SDAT) is a neurodegenerative disease which results in the progressive impairment of memory. Post-mortem autopsies of brain tissue from SDAT patients have shown a marked decrease in cholinergic neurons. Taken together these observations form the basis for the cholinergic hypothesis for memory loss. A series of chemical synthesis projects have been initiated in the geriatric program to discover selective cholinergic agonists to ameliorate the symptons of this degenerative disease.

In this respect, a number of derivatives of the cholinergic agent, oxotremorine, have been synthesized. Resul, B. and coworkers, Eur. J. Med. Chem., 1982, 17, 317 report the synthesis of N-methyl-N-(1-methyl-4-pyrrolidino-2-butynyl)acetamide, referred to as BM-5, which acts as an antagonist at some muscarinic sites while being an agonist at most others. It has been suggested that this type of compound may be useful for the therapy of Alzheimer-type dementia. Lundkvist, J.R.M., et al., J. Med. Chem., 1989, 32, 863–869 synthesized a series of conformationally restricted analogues of BM-5 which differ structurally from those of the present invention.

SUMMARY OF THE INVENTION

This invention is concerned with new compounds described by the following formulas:

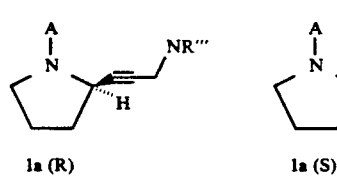

Formula 1

1a (R)    1a (S)

wherein A is selected from hydrogen, ($C_1$–$C_6$)acyl, ($C_1$–$C_6$)alkoxycarbonyl, trihaloacetyl or ($C_1$–$C_6$)alkylsulfonyl; NR''' is equal to NR' and NR''; RN' is equal to pyrrolidino, piperidino, amino, ($C_1$–$C_6$)alkylamino, or ($C_1$–$C_6$)dialkylamino; NR'' is equal to ($C_1$–$C_6$)trialkylamino; with the proviso that when NR' is equal to pyrrolidino or dimethylamino or when NR'' is equal to trimethylamino, A may not be acetyl. The invention is also concerned with methods of treating diseases of the central nervous system in mammals employing these new compounds; with pharmaceutical preparations containing these compounds; and with the processes for the production of these compounds.

DESCRIPTION OF THE INVENTION

The novel compounds of the present invention may be prepared in accordance with the following schemes, wherein A is selected from hydrogen, ($C_1$–$C_6$)-acyl, ($C_1$–$C_6$)alkoxycarbonyl, trihaloacetyl or ($C_1$–$C_6$)alkylsulfonyl; NR''' is equal to NR'' and NR'; NR' is equal to pyrrolidino, piperidino, amino, ($C_1$–$C_6$)alkylamino, or ($C_1$–$C_6$)dialkylamino; NR'' is equal to ($C_1$–$C_6$)trialkylamino; with the proviso that when NR' is equal to pyrrolidino or dimethylamino or when NR'' is equal to trimethylamino, A may not be acetyl.

Scheme I illustrates the synthesis of the derivatives with the (R) absolute configuration.

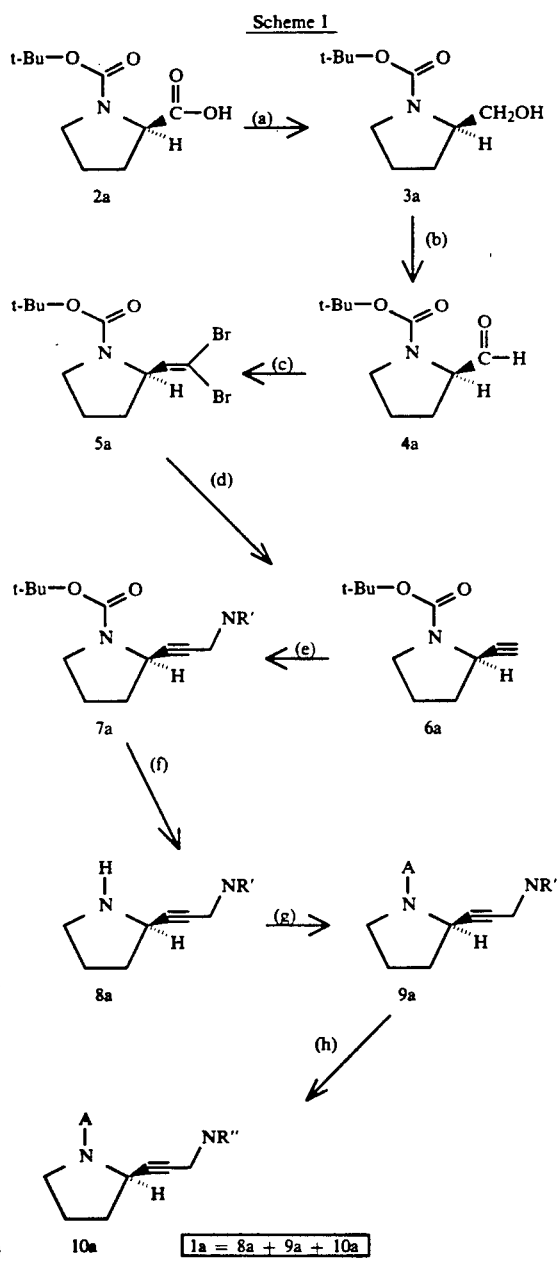

(a) $BH_3 \cdot SMe_2 \cdot THF$
(b) PCC, 4Å Sieves, HOAc, $CH_2Cl_2$
(c) $CBr_4$, $Ph_3P$, $CH_2Cl_2$
(d) sec-BuLi, THF
(e) $(CH_2O)_x$, pyrrolidine, HOAc, CuCl
(f) 2N HCl, EtOH
(g) trihaloacetyl anhydride or chloride, ($C_1$–$C_6$)acylanhydride or chloride, ($C_1$–$C_6$)alkylsulfonyl chloride or $HCO_2H$
(h) ($C_1$–$C_6$)alkylhalide In according with Scheme I, N-α-BOC-D-proline 2a is reacted in an ether solvent such as tetrahydrofuran at a temperature ranging from −2° C. to the reflux temperature of the solvent with 10M boran-methyl sulfide complex to produce (R)-2-(hydroxymethyl)-1-pyrrolidinecarboxylic acid, 1,1-dimethylethyl ester 3a. Compound 3a in a chlorinated hydrocarbon solvent such as methylene chloride is treated with an oxidizing agent such as pyridinium chlorochromate, 4 Å molecular sieves and glacial acetic acid to give (R)-2-formyl-1-pyrrolidinecarboxylic acid 1,1-dimethylethyl ester 4a. Compound 4a in methylene chloride is treated with a methylene chloride solution of triphenylphosphine and carbon tetrabromide to produce (R)-2-(2,2-dibromoethenyl)-1-pyrrolidinecarboxylic acid, 1,1-dimethylethyl ester 5a. The dibromo compound 5a in an ether solvent such as tetrahydrofuran is reacted at −78° C. with an alkyl lithium reagent such as sec-butyllithium to give (R)-2-ethynyl-1-pyrrolidinecarboxylic acid, 1,1-dimethylethyl ester 6a.

The compound of general formula 6a is reacted with paraformaldehyde, acetic acid, copper (I) or (II) chloride and a secondary amine such as pyrrolidine in an ether solvent such as dioxane under an inert atmosphere at the reflux temperature of the solvent to give, on basification, compounds of the general formula 7a. The compound of general formula 7a is reacted with a solution of a strong acid such as 2N hydrochloric acid in an alcohol solvent at or around room temperature to produce a compound of general formula 8a, for example (R)-1-[3-(2-pyrrolidinyl)-2-propynyl]pyrrolidine, dihydrochloride.

The compound of general formula 8a in methylene chloride is treated with either a trihaloacetyl anhydride or chloride, a (C₁-C₆)acyl anhydride or chloride, a (C₁-C₆)alkyl chloroformate, (C₁-C₆) alkylsulfonyl chloride or a mixed formyl acyl anhydride to produce a compound of general formula 9a, for example (R)-2-[3-(1-pyrrolidinyl)-1-propynyl]-1-(trifluoroacetyl)pyrrolidine. hydrochloride.

Scheme II illustrates the synthesis of derivatives with the (S) absolute configuration.

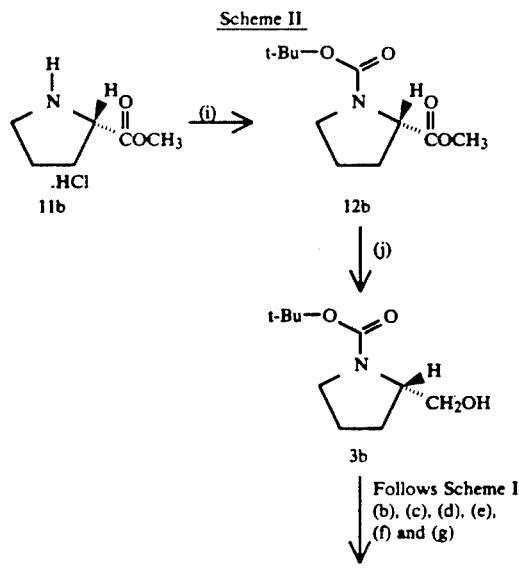

Scheme II

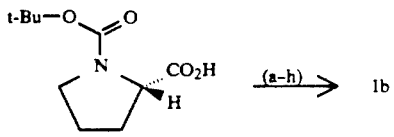

(a) BH₃·SMe₂·THF
(b) PCC, 4Å Sieves, HOAc, CH₂Cl₂
(c) CBr₄, Ph₃P, CH₂CH₂
(d) sec-BuLi, THF
(e) (CH₂O)ₓ, pyrrolidine, HOAc, CuCl
(f) 2N HCl, EtOH
(g) trihaloacetyl anhydride or chloride, (C₁-C₆)acylanhydride or chloride, (C₁-C₆)alkylsulfonyl chloride or HCO₂H
(h) (C₁-C₆)alkylhalide
(i) (t-BuOC)₂O, Et₃N
(j) NaBH₄, LiCl In accordance with Scheme II, proline methyl ester, hydrochloride 11b in methylene chloride is treated with di-tert-butyl dicarbonate in the presence of triethylamine using the method described by B. D. Harris, K. L. Bhat and M. M. Soulie, Heterocycles, 24, 1045 (1986) to produce(S)-1-(1,1-dimethylethyl)-1,2-pyrrolidinecarboxylic acid, 2-methyl ester 12b. Following the procedure in the above reference, compound 12b in tetrahydrofuran is reacted with lithium chloride and sodium borohydride in ethanol to produce (S)-2-(hydroxymethyl)-1-pyrrolidinecarboxylic acid, 1,1-dimethylethyl ester 3b. The remaining (S) compounds are made following Scheme I (b), (c), (d), (e), (f) and (g).

Alternately, in accordance with Scheme II compounds of general formula 1b are prepared in a similar manner to those of general formula 1a using N-α-t-BOC-L-proline as the starting compound with the procedures described in Scheme I.

The novel compounds described herein are useful as cholinergic agents. A chronic deficiency in central cholinergic function has been implicated in a variety of neurologic and psychiatric disorders, including Senile Dementia of the Alzheimer's type (SDAT), tardive dyskinesia, Pick's disease and Huntington's chorea. Postmortem neurochemical investigations of patients with SDAT have demonstrated a reduction in presynaptic markers for acetylcholine-utilizing neurons in the hippocampus and the cerebral cortex. [P. Davies and A. J. R. Maloney, Lancet, 1976-II, 1403, (1976); E. K. Perry, R. H. Perry, G. Blessed, B. E. Tomlinson, J. Neurol. Sci., 34, 247, (1976)]. The basis for this cholinergic abnormality is unclear, but evidence suggests that the cholinergic neurons in the nucleus basalis of Meynert may selectively degenerate in SDAT [J. T. Coyle, D. J. Price, M. R. DeLong, Science, 219, 1184, (1983)]. If this degeneration plays a role in behavior symptoms of the disease, then a possible treatment strategy would be to compensate for the loss of cholinergic output to the cortex and hippocampus.

In an aged monkey animal model, designed to mimic the symptoms of SDAT, the direct muscarinic agonists arecoline [R. T. Bartus, R. L. Dean, B. Beer, Neurobiology of Aging, 1, 145, (1980)] and oxotremorine [R. T. Bartus, R. L. Dean, B. Beer, Psychopharmacology Bulletin, 19, 168, (1983)] produced significant improvement in performance. These results in aged monkeys were corroborated in SDAT patients with arecoline which produced a more-consistent improvement when compared to the anticholinesterase inhibitor physostigmine [J. E. Christie, A. Shering, J. Ferguson, A. M. Glen, British Journal of Psychiatry, 138, 46, (1981)].

These animal behavioral and clinical results have instigated significant efforts in a search for a muscarinic agonist which will selectively compensate for the loss of cholinergic input in the hippocampus and cerebral cortex. However, the search must be refined to seek agonists which will not effect significantly the remaining body cholinergic functions thereby avoiding untoward side effects. The recent disclosure [T. I. Bonner, N. J. Buckley, A. C. Young, M. R. Brann, Science, 237,527, (1987)] that muscarinic receptors are not all the same but exist as a heterogenous population of receptors substantiates the possibility for the discovery of a selective muscarinic agonist.

N-methyl-N-(1-methyl-4-pyrrolidino-2-butynyl)-acetamide (BM-5) has been reported to be a presynaptic cholinergic antagonist (which should disinhibit the release of endogenous acetylcholine) and a postsynaptic partial cholinergic agonist (which should mimic the effects of acetylcholine).

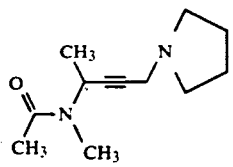

BM-5 (I)

Chemically BM-5 (I) is a fairly flexible molecule that can assume a number of different conformations. The present invention describes the synthesis of a series of 1-substituted-2-(3-amino-1-propynyl)-pyrrolidines which are derivatives of BM-5 in which one degree of freedom (bond c) has been restricted. Generalization of structure (II) provides (III) which represents the target compounds of this invention;

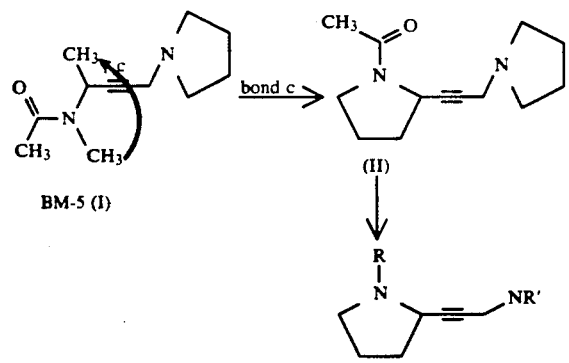

The compounds of this invention were tested for cholinergic activity according to the following procedures.

[³H] Quinuclidinyl Benzilate Binding Assay

This assay is utilized in conjunction with the ³H-Cis-methyldioxolane binding assay to evaluate antagonist and high affinity agonist binding properties of CNS cholinergic agents. The procedure is adapted from Watson, M., Yamamura, H. I., and Roeske, W. R., J. Pharmacol. Exp. Ther. 237: 411–418 (1986) and Watson, M., Roeske, W. R., and Yamamura, H. I., J. Pharmacol. Exp. Ther. 237: 419–427 (1986).

Tissue Preparation

Rats are sacrificed by decapitation and the brain removed and placed on ice. The cerebral cortex is dissected on a cold stage, weighed and homogenized (Polytron, setting 5.5 with PT-10 saw-tooth generator for 15 seconds) in 50 volumes (wet wt/vol) of ice-cold 10 mM (8.1 mM $Na_2HPO_4$, 1.9 mM $KH_2PO_4$) sodium-potassium phosphate buffer (NaKPB), pH 7.4. The homogenate is placed in an ice bath for 30 seconds and homogenized again as above. This procedure is repeated once again for a total of three times. The resulting homogenate is then diluted 1:3000 (original wet wt/vol) with ice-cold NaKPB for use in the assay. The final protein content per 2.0 ml of incubation mixture is 0.1 mg.

Dilution of Compounds

A stock solution of atropine is prepared at 0.2 mM to define non-specific binding (1 µM final conc). Test compounds are prepared at 40 mM (final conc 1 mM) in buffer (if water soluble) or in absolute ethanol - 1N HCl (1:1, v/v) and serially diluted to the desired concentrations. In general, dose-response profiles are examined between 1 mM and 1 pM final concentrations.

Preparation of ³H-QNB

³H-QNB (NEN, NET-656; specific activity=30.0 Ci/mmol) is diluted to 5 nM, with NaPB (final concentration= −0.25 nM activity approximately 18,000 cpm at a counting efficiency of 55%).

³H-QNB Binding Assay

A typical protocol is outlined below

| Tube No. | ID* | Buffer µL | Atropine µL | Test Compound µL | ³H-QNB µL | Tissue ml |
|---|---|---|---|---|---|---|
| 1-2 | Total | 50 | — | — | 100 | 1.85 |
| 3-4 | NS | 40 | 10 | — | " | " |
| 5-6 | 4e-11 | — | — | 50 | " | " |
| 7-8 | 4e-10 | — | — | " | " | " |
| 9-10 | 4e-09 | — | — | " | " | " |
| 11-12 | 4e-08 | — | — | " | " | " |
| 13-14 | 4e-07 | — | — | " | " | " |
| 15-16 | 4e-06 | — | — | " | " | " |
| 17-18 | 4e-05 | — | — | " | " | " |
| 19-20 | 4e-04 | — | — | " | " | " |
| 21-22 | 4e-03 | — | — | " | " | " |
| 23-24 | 4e-02 | — | — | " | " | " |

*Stock concentration [M] of compound to be tested.

Components are added in the following order: test compound, radioligand, buffer or tissue to give a final volume of 2.0 ml. After adding the tissue homogenate, the tubes are thoroughly mixed and incubated at 25° C. for 120 minutes. At the end of 120 minutes, the samples are filtered through GF/B glass fiber filters (Whatman) using a 24 sample cell harvester (Brandel) under a vacuum of 15 mm Hg. The tubes are washed with 5×3 ml ice-cold NaKPB. The filters are then placed in scintillation vials with 10 ml of scintillation cocktail (Beckman HP or HP/B), allowed to stand overnight, shaken and then counted. Specific binding is calculated as Total - NS (non-specific). The percent inhibition of specific binding is then calculated and the IC50 values computed using either the LIGAND or LUNDON software packages for competition binding. The results of

[³H]-Cis-methyldioxolane (³H-CD) Binding Assay (High Affinity)

This assay is utilized in conjunction with ³H-QNB binding to evaluate high affinity agonist binding and antagonist properties of CNS cholinergic agents. The procedure is adapted from Vickroy, T. W., Roeske, W. R., and Yamamura, H. I., J. Pharmacol. Exp. Ther. 229: 747-755 (1984). This is a rapid filtration assay that is set up to label only the high affinity agonist conformation of the muscarinic cholinergic receptor.

Tissue Preparation

Rats are sacrificed by decapitation and the brain removed and placed on ice. The cerebral cortex is dissected on a cold stage, weighed and homogenized (Polytron, setting 5.5 with Pt-10 saw-tooth generator for 15 seconds in 50 volumes (wet wt/vol) of ice-cold 10 mM (8.1 mM $Na_2HPO_4$, 1.9 mM $KH_2PO_4$) sodium-potassium phosphate buffer (NaKPB), pH 7.4. The homogenate is placed in an ice bath for 30 seconds and homogenized again as above. This procedure is repeated once again for a total of three times. The resulting homogenate is then diluted 1:300 (original wet wt/vol) with ice-cold NaKPB for use in the assay. The final protein content per 2.0 ml of incubation mixture is 0.75 mg.

Dilution of Compounds

A stock solution of atropine is prepared at 0.2 mM to define non-specific binding 1 lM final conc). Test compounds are prepared at 40 mM (final conc 1 mM) in buffer (if water soluble) or in absolute ethanol - 1N HCl (1:1, v/v) and serially diluted to the desired concentrations. In general, dose-response profiles are examined between 1 mM and 1 pM final concentrations.

Preparation of ³H-CD

³H-CD (NEN, NET-647; specific activity=55.5 Ci/mmol) is diluted to 20 nM with NaPB (final conc=1.0 nM, activity approximately 75,000 cpm at a counting efficiency of 55%).

Technical Notes

³H-CD adheres readily to both glass and plastic surfaces. To eliminate this problem (and the chance for introducing artifacts into the results), stock vials, pipette tips and all glass tubes are routinely treated with Prosil-28, a siliconizing agent, and oven dried prior to use in an assay. Additionally, the GF/B glass fiber filters are pre-soaked in an aqueous polyethylenimine (PEI) solution (0.1%, pH 7.0) prior to use.

All points in the inhibition curve (including total and non-specific binding) are always measured on single PEI treated filter strips to minimize filter-to-filter variability. (See Bruns, R. F., et al. Anal. Biochem. 132: 74-81 (1983) for the use of PEI treated filters in filtration receptor assays).

The ³H-CD is prepared fresh in buffer just prior to use in the assay to avoid possible decomposition. It should be kept on an ice bath after dilution in buffer.

³H-CD Binding Assay

A typical protocol is outlined below:

| Tube No. | ID* | Buffer μL | Atropine μL | Test Compound μL | ³H-CD μL | Tissue ml |
|---|---|---|---|---|---|---|
| 1-2 | Total | 50 | — | — | 100 | 1.85 |
| 3-4 | NS | 40 | 10 | — | " | " |
| 5-6 | 4e-11 | — | — | 50 | " | " |
| 7-8 | 4e-10 | — | — | " | " | " |
| 9-10 | 4e-09 | — | — | " | " | " |
| 11-12 | 4e-08 | — | — | " | " | " |
| 13-14 | 4e-07 | — | — | " | " | " |
| 15-16 | 4e-06 | — | — | " | " | " |
| 17-18 | 4e-05 | — | — | " | " | " |
| 19-20 | 4e-04 | — | — | " | " | " |
| 21-22 | 4e-03 | — | — | " | " | " |
| 23-24 | 4e-02 | — | — | " | " | " |

*Stock concentration [M] of compound to be tested.

Components are added in the following order: compound, radioligand, buffer or tissue to give a final volume of 2.0 ml. After adding the tissue homogenate, the tubes are thoroughly mixed and incubated at 25° C. for 120 minutes. At the end of 120 minutes, the samples are filtered through PEI pretreated GF/B glass fiber filters (Whatman) using a 24 sample cell harvester (Brandel) under a vacuum of 15 mm Hg. The tubes are washed with 5×3 ml ice-cold NaKPB. The filters are then placed in scintillation vials with 10 ml of scintillation cocktail (Beckman HP or HP/B), allowed to stand overnight, shaken and then counted. Specific binding is calculated as Total - NS (non-specific). The percent inhibition of specific binding is then calculated and the IC50 values computed using either the LIGAND or LUNDON software packages for competition binding. The results of this test on representative compounds of this invention appear in Table I.

TABLE I

| Compound | ³H-QNB IC$_{50}$ μM | ³H-CD IC$_{50}$ nM |
|---|---|---|
| (R)-2-[3-(1-Pyrrolidinyl)-1-propynyl]-1-pyrrolidinecarboxaldehyde | 34 | 3,583 |
| (S)-2-[3-(1-Pyrrolidinyl-1-propynyl]-1-pyrrolidinecarboxaldehyde | 65 | 5,235 |
| (S)-2-[3-(1-Pyrrolidinyl)-1-propynyl]-1-pyrrolidinecarboxaldehyde, hydrochloride | 88 | 11,077 |
| (R)-1-Acetyl-2-[3-(1-pyrrolidinyl)-1-propynyl]pyrrolidine | 8.8 | 780 |
| (S)-1-Acetyl-2-[3-(1-pyrroldinyl)-1-propynyl]pyrrolidine | 76 | 2,713 |
| (S)-1-Acetyl-2-[3-(1-pyrrolidinyl)-1-propynyl]pyrrolidine, hydrochloride | 73 | 3,262 |
| (R)-1-[3-(2-Pyrrolidinyl)-2-propynyl]pyrrolidine | 3.1 | 514 |
| (R)-1-[3-(2-Pyrrolidinyl)-2-propynyl]pyrrolidine, dihydrochloride | 2.7 | 742 |
| (S)-2-[3-(1-Pyrrolidinyl)-1-propynyl]-1-(trifluoroacetyl)-pyrrolidine | 18 | 5,473 |
| (S)-2-[3-(1-Pyrrolidinyl)-1-(trifluoroacetyl)pyrrolidine, hydrochloride | 16 | 3,834 |
| (R)-1-(Methylsulfonyl)-2-[3-(1-pyrrolidinyl)-1-propynyl]-pyrrolidine | 23 | 973 |
| (R)-1-(Methylsulfonyl)-2-[3-(1-pyrrolidinyl)-1-propynyl]-pyrrolidine, hydrochloride | 25 | 2,448 |
| (S)-1-(Methylsulfonyl)-2-[3-(1-pyrrolidinyl)-1-propynyl]-pyrrolidine | 43 | 6,784 |
| (S)-1-(Methylsulfonyl)-2-[3-(1- | 47 | 8,078 |

TABLE I-continued

| Compound | $^3$H-QNB IC$_{50}$ μM | $^3$H-CD IC$_{50}$ nM |
|---|---|---|
| pyrrolidinyl)-1-propynyl]-pyrrolidine, hydrochloride | | |
| (R)-2-[3-(1-Pyrrolidinyl)-1-propynyl]-1-pyrrolidinecarboxylic acid, 1,1-dimethylethyl ester | 6.5 | 29 |
| (S)-2-[3-(1-Pyrrolidinyl)-1-propynyl]-1-pyrrolidinecarboxylic acid, 1,1-dimethylethyl ester | 4.2 | 247 |
| (R)-2-[3-(1-Pyrrolidinyl)-1-propynyl]-1-(trifluoroacetyl)-pyrrolidine | 40 | 2,577 |
| (R)-2-[3-(1-Pyrrolidinyl)-1-propynyl]-1-(trifluoroacetyl)-pyrrolidine, dihydrochloride | 43 | 8,571 |

Those compounds which have $^3$H-CD IC$_{50}$ values of <1000 nM and/or $^3$H-QNB IC$_{50}$ values of <1000 uM are considered active. Those substituents which show weak activity or are inactive by these criteria may be considered pro-drugs for the more active substituents.

The pharmaceutical preparations of the present invention may contain, for example, from about 0.5% up to about 90% of the active ingredient in combination with the carrier, more usually between 5% and 60% by weight.

The effective dosage of active ingredient employed may vary with the particular compound employed, the mode of administration, and the severity of the condition being treated. In general, however, satisfactory results are obtained when the compounds of the invention are administered at a daily dosage of from about 0.02 mg to about 100 mg/kg of patient body weight, preferably given in divided doses two to four times a day, or in sustained release form. For most patients, the total daily dosage is from about 1 mg to about 5,000 mg, preferably from about 1 mg to 20 mg. Dosage forms suitable for internal use comprise from about 0.25 to 5.0 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

A decided practical advantage is that these active compounds may be administered orally as well as by intravenous, intramuscular, or subcutaneous routes if necessary. Solid carriers include starch, lactose, dicalcium phosphate, microcrystalline cellulose, sucrose, and kaolin, while liquid carriers include sterile water, polyethylene glycols, non-ionic surfactants, and edible oils such as corn, peanut, and sesame oils, as are appropriate to the nature of the active ingredient and the particular form of administration desired. Adjuvants customarily employed in the preparation of pharmaceutical compositions may be advantageously included, such as flavoring agents, coloring agents, and antioxidants, e.g., vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exits. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in therapeutic compositions is contemplated.

The following examples describe in detail the chemical synthesis of representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperatures, solvents, and/or reagents could increase the yields.

EXAMPLE 1

(R)-2-(Hydroxymethyl)-1-pyrrolidinecarboxylic acid, 1,1-dimethylethyl ester

To a solution of 25.0 g of N-α-t-BOC-D-proline in 250 ml of tetrahydrofuran which is cooled to 0° C. is added dropwise 15 ml of 10M borane-methyl sulfide complex. The reaction is kept at around −20° C. during the addition followed by warming to room temperature and then is gently refluxed for one hour. The mixture is cooled to 0° C., 250 ml of methanol is added carefully and the reaction is evaporated in vacuo to give 23.3 g of a colorless oil which crystallizes on standing to a colorless solid, mp 50°-53° C., $[\alpha]_D^{26°} = +47° \pm 1$ (C=1.162%, methylene chloride).

EXAMPLE 2

(R)-2-Formyl-1-pyrrolidinecarboxylic acid, 1,1-dimethylethyl ester

To a water cooled (25° C.) solution of 10.0 g of (R)-2-(hydroxymethyl)-1-pyrrolidinecarboxylic acid, 1,1-dimethylethyl ester in 250 ml of dry methylene chloride is added in one portion 16.0 g of pyridinium chlorochromate, 36.0 g of dried, crushed 4 Å molecular sieves and 4.5 ml of glacial acetic acid. The resulting mixture is stirred at 25° C. for one hour. Twenty-five grams of diatomaceous earth and 500 ml of diethyl ether is added, the suspension is filtered through a pad of diatomaceous earth and the filtrate concentrated in vacuo. The residue is dissolved in diethyl ether and is passed through a short column of silica gel using diethyl ether as the eluant. The first two 500 ml fractions contain the desired aldehyde. The solvent is concentrated in vacuo to give 10.1 g of desired product.

EXAMPLE 3

(R)-2-(2,2-Dibromoethenyl)-1-pyrrolidinecarboxylic acid, 1,1-dimethylethyl ester To a solution of 40.0 g of triphenylphosphine and 26.0 g of carbon tetrabromide in 700 ml of dry methylene chloride, which is cooled to 0° C., is added dropwise a solution of 10.1 g of (R)-2-formyl-1-pyrrolidinecarboxylic acid, 1,1-dimethylethyl ester in 20 ml of dry methylene chloride. The reaction is stirred for 30 minutes, a solution of saturated aqueous sodium bicarbonate is added and the layers are separated. The organic layer is filtered and concentrated in vacuo. The residue is chromatographed using silica gel as absorbant to give 10.0 g of the product as colorless crystals, mp 55°-60° C., $[\alpha]_D^{26°} = -22° \pm 1$ (C=1.149%, methylene chloride).

EXAMPLE 4

(R)-2-Ethynyl-1-pyrrolidinecarboxylic acid, 1,1-dimethylethyl ester

A solution of 7.0 g of (R)-2-(2,2-dibromoethenyl)-1-pyrrolidinecarboxylic acid, 1,1-dimethylethyl ester in 75 ml of dry tetrahydrofuran is cooled to −78° C. under an atmosphere of argon and treated with 33.1 ml of sec-butyllithium over 45 minutes. The resulting solution is stirred at −78° C. for one hour. The reaction mixture is treated with 100 ml of saturated ammonium chloride, warmed to room temperature, diluted with 300 ml of diethyl ether and the layers are separated. The organic layer is washed with 150 ml of saturated sodium chloride, dried over sodium sulfate and concentrated in vacuo. A 0.72 g aliquot of the product is purified by chromatography using silica gel as absorbant to give 0.55 g of the product as a colorless oil, $[\alpha]_D^{26°} = +84° \pm 1$ (C=1.049%, methylene chloride).

EXAMPLE 5

(R)-2-[3-(1-Pyrrolidinyl)-1-propynyl]-1-pyrrolidinecarboxylic acid, 1,1-dimethylethyl ester A mixture of 3.5 g of (R)-2-ethynyl-1-pyrrolidinecarboxylic acid, 1,1-dimethylethyl ester, 75 ml dry dioxane, 3.0 ml pyrrolidine, 1.43 g of paraformaldehyde, 7.0 ml of glacial acetic acid and 50 mg of cuprous chloride is stirred at room temperature for 15 minutes then refluxed for 2 hours. The reaction is cooled and concentrated in vacuo. The residue is partitioned between water and methylene chloride and the pH of the mixture is adjusted to pH 11 with ammonium hydroxide. The basified reaction is extracted with methylene chloride and dried over sodium sulfate. The methylene chloride solution is passed over hydrous magnesium silicate and concentrated in vacuo to give 5.65 g of a dark yellow oil. The product is purified by chromatography using deactivated alumina as the absorbant, to give 0.55 g of the product as a pale yellow oil, $[\alpha]_D^{26°} = +100.6° \pm 0.8$ (C=1.22%, methylene chloride).

EXAMPLE 6

(R)-1-[3-(2-Pyrrolidinyl)-2-propynyl]pyrrolidine, dihydrochloride

A mixture of 7.0 g of (R)-2-[3-(1-pyrrolidinyl)-1-propynyl]-1-pyrrolidinecarboxylic acid, 1,1-dimethylethyl ester, 61 ml of ethanol and 61 ml of 2N hydrochloric acid is heated at 80° C. for one hour. The reaction is concentrated in vacuo and the residue is extracted with methylene chloride. The aqueous layer is concentrated in vacuo, made basic with 10N sodium hydroxide and extracted with methylene chloride. The methylene chloride solution is dried over sodium sulfate, filtered and concentrated in vacuo. The residue is dissolved in methanol, treated with an excess of methanolic hydrogen chloride and precipitated with the addition of diethyl ether. The dihydrochloride is recrystallized from hot methanol to give pure product, mp 198°-200° C. with decomposition, $[\alpha]_D^{26°} = +21° \pm 1$ (C=1.012%, methanol).

EXAMPLE 7

(R)-2-[3-(1-Pyrrolidinyl)-1-propynyl]-1-(trifluoroacetyl)pyrrolidine, hydrochloride To a solution of 0.63 g of (R)-1-[3-(2-pyrrolidinyl)-2-propynyl]pyrrolidine in 10 ml of methylene chloride which is cooled to 0° C. is added 2.0 ml of trifluoroacetic anhydride. The reaction is stirred at room temperature for 2 hours, treated with 5 ml of methanol, washed with sodium bicarbonate and dried over sodium sulfate. The organic layer is passed over a thin pad of hydrous magnesium silicate and the filtrate is concentrated in vacuo. The residue is treated with an excess of methanolic hydrogen chloride and the product is precipitated by the addition of ether to give the product as colorless crystals, mp 156°-157° C., $[\alpha]_D^{26°} = +103° \pm 1$ (C=1.160%, methanol).

EXAMPLE 8

(R)-1-Acetyl-2-[3-(1-pyrrolidinyl)-1-propynyl]-pyrrolidine, hydrochloride

Following the procedure of Example 7, 0.63 g of (R)-1-[3-(2-pyrrolidinyl)-2-propynyl]pyrrolidine in 10 ml of methylene chloride is treated with 1.33 ml of acetic anhydride. The hydrochloride salt of the product is obtained as a yellow oil, $[\alpha]_D^{26°} = +85° \pm 1$ (C=1.137%, methanol).

EXAMPLE 9

(R)-1-(Methylsulfonyl)-2-[3-(1-pyrrolidinyl)-1-propynyl]pyrrolidine, hydrochloride Following the procedure of Example 7, 0.65 g of (R)-1-[3-(2-pyrrolidinyl)-2-propynyl]pyrrolidine in 5 ml of methylene chloride is treated with 0.31 ml of methanesulfonyl chloride. The product is purified by chromatography using deactivated alumina as the absorbant to give the product as colorless crystals. The hydrochloride salt of the product is obtained as colorless crystals, mp 198°-199° C. (dec), $[\alpha]_D^{26°} = +78° \pm 1$ (C=1.020%, methanol).

EXAMPLE 10

(R)-2-[3-(1-Pyrrolidinyl)-1-propynyl]-1-pyrrolidinecarboxaldehyde

To a solution of 0.58 g of (R)-1-[3-(2-pyrrolidinyl)-2-propynyl]pyrrolidine in 6.9 ml of formic acid is added dropwise at room temperature 2.3 ml of acetic anhydride. The reaction is stirred for 30 minutes, followed by the addition of 10 ml of ice water. The resulting mixture is concentrated in vacuo and the residue treated with a solution of saturated sodium bicarbonate. The aqueous layer is extracted with methylene chloride, dried over sodium sulfate and concentrated in vacuo to a yellow oil. The product is purified by chromatography using deactivated alumina as the absorbant to give 0.65 g of a light yellow oil, $[\alpha]_D^{26°} = +99° \pm 1$ (C=1.008%, methylene chloride).

EXAMPLE 11

(S)-1-(1,1-Dimethylethyl)-1,2-pyrrolidinecarboxylic acid, 2-methyl ester

Following the procedure of B. D. Harris, K. L. Bhat and M. M. Soulie, Heterocycles, 24, 1045 (1986), 36.9 g of L-proline methyl ester hydrochloride, 62 ml of triethyl amine, 61 ml of di-tert-butyl dicarbonate and 250 ml of methylene chloride is reacted to give 42 g of the desired product as an oil, $[\alpha]_D^{26°} = -58° \pm 1$ (C=1.125%, chloroform). Literature rotation $[\alpha]_D^{26°} = -54° \pm 1$ (C=3.67%, chloroform).

EXAMPLE 12

(S)-2-(Hydroxymethyl)-1-pyrrolidinecarboxylic acid, 1,1-dimethylethyl ester

Following the procedure of B. D. Harris, K. L. Bhat, and M. M. Soulie, Heterocycles, 24, 1045 (1986), 6.83 g of lithium chloride, 6.09 g of sodium borohydride (pellets), 115 m. of ethanol and 18.4 g of (S)-1-(1,1-dimethylethyl)-1,2-pyrrolidinecarboxylic acid, 2-methyl ester in 80 ml of tetrahydrofuran is reacted to give 14.0 g of the desired product as white crystals, mp 58°-59° C., $[\alpha]_D^{26°} = -50° \pm 1$ (C=1.05%, chloroform). Literature rotation $[\alpha]_D^{26°} = -48° \pm 1$ (C=1.2%, chloroform).

EXAMPLE 13

(S)-2-Formyl-1-pyrrolidinecarboxylic acid, 1,1-dimethylethyl ester

Following the procedure of Example 2, 16.0 g of pyridinium chlorochromate, 10.0 g of (S)-2-(hydroxymethyl)-1-pyrrolidinecarboxylic acid, 1,1-dimethylethyl ester, 36.0 g of crushed 4 Å molecular sieves and 4.5 ml of glacial acetic acid in 250 ml of methylene chloride gives 6.8 g of the product as a yellow oil.

EXAMPLE 14

(S)-2-(2,2-Dibromoethenyl-1-pyrrolidinecarboxylic acid, 1,1-dimethylethyl ester

Following the procedure of Example 3, 6.8 g of (S)-2-formyl-1-pyrrolidinecarboxylic acid, 1,1-dimethylethyl ester in 20 ml of methylene chloride is reacted with 40 g of triphenylphosphine, 26 g of carbon tetrabromide in 700 ml of methylene chloride to give 5.8 g of the desired product as a colorless solid, mp 58°-59° C., $[\alpha]_D^{26°} = +24° \pm 1$ (C=1.048%, methylene chloride).

EXAMPLE 15

(S)-2-Ethynyl-1-pyrrolidinecarboxylic acid, 1,1-dimethylethyl ester

Following the procedure of Example 4, 10.0 g of (S)-2-(2,2-dibromoethenyl)-1-pyrrolidinecarboxylic acid, 1,1-dimethylethyl ester in 150 ml of dry tetrahydrofuran, is reacted with 45.5 ml of sec-butyl-lithium to give 3.0 g of the product as a yellow oil, $[\alpha]_D^{26°} = -81° \pm 1$ (C=0.974%, methylene chloride).

EXAMPLE 16

(S)-2-[3-(1-Pyrrolidinyl)-1-propynl]-1-pyrrolidinecarboxylic acid, 1,1-dimethylethyl ester Following the procedure of Example 5, a mixture of 5.30 g of (S)-2-ethynyl-1-pyrrolidinecarboxylic acid, 1,1-dimethylethyl ester, 4.50 ml of pyrrolidine, 2.20 g of paraformaldehyde, 10.0 ml of glacial acetic acid, 0.10 g of cuprous chloride and 80 ml of dioxane is heated to give 6.62 g of the product as a yellow oil, $[\alpha]_D^{26°} = -100° \pm 1$ (C=1.042%, methylene chloride).

EXAMPLE 17

(S)-1-[3-(2-Pyrrolidinyl)-2-propynyl]pyrrolidine, dihydrochloride

Following the procedure of Example 6, a mixture of 6.62 g of (S)-2-[3-(1-pyrrolidinyl)-1-propynl]-1-pyrrolidinecarboxylic acid, 1,1-dimethylethyl ester, 59.4 ml of 2N hydrochloric acid and 60 ml of ethanol is reacted to give 2.50 g of the product as colorless crystals, mp 196°-197° C. with decomposition, $[\alpha]_D^{26°} = -20° \pm 1$ (C=1.047%, methanol).

EXAMPLE 18

(S)-2-[3-(1-Pyrrolidinyl)-1-propynyl]-1-trifluoroacetyl)-pyrrolidine, hydrochloride Following the procedure of Example 7, a mixture of 0.71 g of (S)-1-[3-(2-pyrrolidinyl)-2-propynyl]-pyrrolidine, 2.25 ml of trifluoroacetic acid and 12 ml of methylene chloride is reacted to give 0.81 g of the product as a pale yellow oil, $[\alpha]_D^{26°} = -125° \pm 1$ (C=1.098%, methylene chloride). A 0.30 g aliquot of the product is treated with an excess of methanolic hydrogen chloride. The resulting salt is crystallized from methanol/ether to give 0.20 g of colorless crystals, mp 156°-157° C., $[\alpha]_D^{26°} = -102° \pm 1$ (C=1.030%, methanol).

EXAMPLE 19

(S)-1-Acetyl-2-[3-(1-pyrrolidinyl)-1-propynyl]-pyrrolidine, hydrochloride

Following the procedure of Example 7, 0.71 g of (S)-1-[3-(2-pyrrolidinyl)-2-propynyl]pyrrolidine in 20 ml of methylene chloride is treated with 1.50 ml of acetic anhydride to give the product as a pale yellow oil, $[\alpha]_D^{26°} = -117° \pm 1$ (C=1.031%, methylene chloride). The hydrochloride salt of the product is obtained as colorless crystals, $[\alpha]_D^{26°} = -103° \pm 1$ (C=1.060%, methanol).

EXAMPLE 20

(S)-1-(Methylsulfonyl)-2-[3-(1-pyrrolidinyl)-1-propynyl]pyrrolidine, hydrochloride Following the procedure of Example 7, 0.58 g of (S)-1-[3-(2-pyrrolidinyl)-2-propynyl]pyrrolidine in 20 ml of methylene chloride is treated with 0.28 ml of methanesulfonyl chloride to give the product as a pale yellow oil, $[\alpha]_D^{26°} = -81° \pm 1$ (C=1.136%, methanol). The hydrochloride salt of the product is obtained as colorless crystals, mp 198°-199° C., $[\alpha]_D^{26°} = -85° \pm 1$ (C=1.129%, methylene chloride).

EXAMPLE 21

(S)-2-[3-(1-Pyrrolidinyl)-1-propynyl]-1-pyrrolidinecarboxaldehyde, hydrochloride Following the procedure of Example 7, 1.30 g of (S)-1-[3-(2-pyrrolidinyl-2-propynyl]pyrrolidine in 15.5 ml of formic acid is treated with 5.2 ml of acetic anhydride to give the product as a pale yellow oil, $[\alpha]_D^{26°} = -126° \pm 1$ (C=1.71%, methylene chloride). The hydrochloride salt of the product is obtained as a yellow oil, $[\alpha]_D^{26°} = -104° \pm 1$ (C=1.113%, methanol).

EXAMPLE 22

(R)-2-[3-(1-Pyrrolidinyl)-1-propynyl]-1-pyrrolidinecarboxylic acid, methyl ester To a stirred solution of 0.60 g of (R)-1-[3-(2-pyrrolidinyl)-2-propynyl]pyrrolidine in 10 ml of ether is added dropwise solutions of 0.35 g of methyl chloroformate in 5 ml of ether and 0.74 ml 5N sodium hydroxide. The reaction is stirred for 30 minutes at 0° C. and diluted with ether. The organic layer is separated and the aqueous layer is extracted with methylene chloride. The combined methylene chloride extracts are dried over sodium sulfate and concentrated in vacuo to give 0.65 g of the crude product as a pale yellow oil. The residue is purified by column chromatography using deactivated alumina as absorbent to give 0.55 of the product as a pale yellow oil, $[\alpha]_D^{26°} = +112° \pm 1$ (C=1.011%, methylene chloride).

EXAMPLE 23

(S)-2-[3-(1-Pyrrolidinyl)-1-propynyl]-1-pyrrolidinecarboxylic acid, methyl ester Following the procedure of Example 22, a mixture of 0.5 g of (S)-1-[3-(2-pyrrolidinyl)-2-propynyl]-pyrrolidine, 0.29 g of methyl chloroformate and 0.60 ml 5N sodium hydroxide in 15 ml of ether is reacted to give 0.50 g of the product as a pale yellow oil, $[\alpha]_D^{26°} = -131° \pm 1$ (C=1.037%, methylene chloride).

EXAMPLE 24

(R)-2-[3-(1-Pyrrolidinyl)-1-propynyl]-1-pyrrolidinecarboxylic acid, ethyl ester

Following the procedure of Example 22, a mixture of 0.60 g of (R)-1-[3-(2-pyrrolidinyl)-2-propynyl]-pyrrolidine, 0.40 g of ethyl chloroformate and 0.75 ml 5N sodium hydroxide in 15 ml of ether is reacted to give 0.62 g of the product as a pale yellow oil, $[\alpha]_D^{26°} = +109° \pm 1$ (C=1.072%, methylene chloride).

EXAMPLE 25

(S)-2-[3-(1-Pyrrolidinyl)-1-propynyl]-1-pyrrolidinecarboxylic acid, ethyl ester

Following the procedure of Example 22, a mixture of 0.5 g of (S)-1-[3-(2-pyrrolidinyl)-2-propynyl]-pyrrolidine, 0.33 g of ethyl chloroformate and 0.6 ml 5N sodium hydroxide in 15 ml of ether is reacted to give 0.5 g of the product as a pale yellow oil, $[\alpha]_D^{26°} = -123° \pm 1$ (C=1.111%, methylene chloride).

We claim:

1. A compound of the formula:

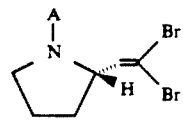

wherein A is t-butoxycarbonyl

2. A compound of the formula:

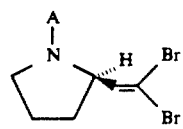

wherein A is t-butoxycarbonyl

3. A compound of the formula:

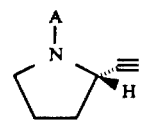

wherein A is t-butoxycarbonyl

4. A compound of the formula:

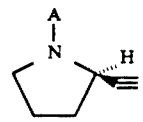

wherein A is t-butoxycarbonyl.

* * * * *